(12) United States Patent
Aichinger et al.

(10) Patent No.: US 6,353,130 B1
(45) Date of Patent: Mar. 5, 2002

(54) METHOD FOR CONTINUOUS PRODUCTION OF (METH)ACRYLIC ALKYL ESTERS

(75) Inventors: Heinrich Aichinger, Mannheim; Holger Herbst, Frankenthal; Gerhard Nestler; Jürgen Schröder, both of Ludwigshafen, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/830,565

(22) PCT Filed: Nov. 5, 1999

(86) PCT No.: PCT/EP99/08475

§ 371 Date: May 7, 2001

§ 102(e) Date: May 7, 2001

(87) PCT Pub. No.: WO00/27788

PCT Pub. Date: May 18, 2000

(30) Foreign Application Priority Data

Nov. 11, 1998 (DE) .......................................... 198 51 983

(51) Int. Cl.[7] .............................................. C07C 69/52
(52) U.S. Cl. ....................................... 560/205; 560/205
(58) Field of Search ......................................... 560/205

(56) References Cited

U.S. PATENT DOCUMENTS

| 5,811,574 A | | 9/1998 | Exner et al. |
| 5,900,125 A | | 5/1999 | Exner et al. |
| 5,945,560 A | * | 8/1999 | Iffland et al. |

FOREIGN PATENT DOCUMENTS

| DE | 195 47 485 | 5/1996 |
| DE | 195 36 178 | 4/1997 |
| DE | 196 04 252 | 8/1997 |
| DE | 198 14 421 | 10/1999 |
| DE | 198 14 449 | 10/1999 |

* cited by examiner

Primary Examiner—Paul J. Killos
Assistant Examiner—Farhard Forohar
(74) Attorney, Agent, or Firm—Oblon, Spivak, McClelland, Maier & Neustadt, P.C.

(57) ABSTRACT

A method for continuous production of (meth)acrylic alkyl esters by reacting (meth)acrylic acid with alkanols containing 1–8 C-atoms, whereby raw (meth)acrylic acid containing acetic acid is used as a starting compound and the alkyl acetate that is formed as a by-product is evacuated in an appropriate area.

22 Claims, No Drawings

METHOD FOR CONTINUOUS PRODUCTION OF (METH)ACRYLIC ALKYL ESTERS

The present invention relates to a process for the continuous preparation of alkyl esters of (meth)acrylic acid by reacting (meth)acrylic acid with alkanols of 1 to 8 carbon atoms in a solvent-free phase at elevated temperatures and in the presence of an acidic esterification catalyst, in which the (meth)acrylic acid, the alkanol and the acid catalyst are fed to a reaction zone, the resulting water as part of a mixture comprising starting alkanol is removed from the reaction mixture by rectification, during the residence time in the reaction zone, in a rectification unit I mounted on the reaction zone, the distillate obtained is separated into an organic phase containing starting alkanol and into a water-containing aqueous phase, the organic phase and, if required, a part of the aqueous phase are recycled to the rectification unit I, the reaction mixture containing the desired ester is passed from the reaction zone into a separation zone comprising further rectification units and the resulting alkyl ester of (meth)acrylic acid is isolated in said separation zone.

The term "(meth)acrylic" is used herein as abbreviated notation for "acrylic or methacrylic".

Alkyl esters of (meth)acrylic acid are generally known and are important, for example, as reactive monoethylenically unsaturated monomers for the preparation of aqueous polymer dispersions by the free radical aqueous emulsion polymerization method, which dispersions are used, for example, as adhesives.

Usually, the preparation of the alkyl (meth)acrylates is carried out by direct, acid-catalyzed reaction (esterification) of (meth)acrylic acid with the corresponding alkanols.

One route for the industrial production of (meth)acrylic acid is the catalytic gas-phase oxidation of suitable $C_3$-/$C_4$-precursors (e.g. propylene, acrolein, isobutene or methacrolein) with molecular oxygen. However, this procedure gives not pure (meth)acrylic acid but a gas mixture which, in relation to (meth)acrylic acid, contains, inter alia, acetic acid as a byproduct, the separation of which from (meth)acrylic acid, in particular by rectification, is expensive (cf. for example DE-A 19814449 and DE-A 19814421).

On the other hand, direct esterification of (meth)acrylic acid with alkanols is carried out predominantly by a method in which, with continuous removal of the water of reaction by distillation, the product ester too is separated from the reaction mixture. The distillate is then separated into an aqueous phase and into an organic phase which contains the desired ester and from which the desired ester must be isolated. The latter is usually carried out by separation steps involving rectification (cf. for example DE-A 19536178). The presence of an organic solvent as an azeotropic water entrainer does not require such an esterification procedure.

With the use of (meth)acrylic acid containing acetic acid (known as crude (meth)acrylic acid), however, the corresponding alkyl ester of acetic acid is unavoidably formed as a byproduct and as part of the abovementioned organic phase in the course of a direct esterification.

However, alkyl acetates as impurities in alkyl (meth)acrylates prove to be troublesome in many fields of use of alkyl (meth)acrylates since they are on the one hand not susceptible to free radical polymerization and, on the other hand, are relatively highly volatile.

In the preparation of aqueous polymer dispersions containing alkyl (meth)acrylates as polymerized units, for example, aqueous polymer dispersions containing free alkyl acetate would be obtained. Owing to the generally good solubility of the alkyl acetate in the polymer particles present in dispersed form in the aqueous polymer dispersion, subsequent removal of alkyl acetate, for example by stripping with air or steam, is possible only with difficulty and by expensive procedures. On the other hand, the alkyl acetate partial pressure of aqueous polymer dispersions containing alkyl acetate is sufficiently high to result in alkyl acetate workplace concentrations which are not completely safe in the atmosphere surrounding the place of processing of the polymer dispersion, and it is for this reason that polymerizers generally demand essentially alkyl acetate-free alkyl (meth)acrylate as starting material for their polymerizations.

On the route to such alkyl acetate-free alkyl (meth)acrylates, the high separation efficiency (i.e. a high reflux ratio and/or a large number of theoretical plates), which promotes both separation of alkyl (meth)acrylates and alkyl acetates by rectification, in particular in the presence of alkanol and water, and separation of the acetic acid from (meth)acrylic acid by rectification, can if necessary be circumvented in a manner known per se by carrying out the separation by rectification with reduced separation efficiency in a singly unsharp manner.

The term "singly unsharp" rectification refers to a rectification in which a mixture which contains two or more components is rectified under conditions (e.g. low reflux ratio and/or a small number of theoretical plates) such that only "one" component of the mixture is obtained in high purity. In the simplest case, this means that, instead of separating a mixture consisting of A (e.g. n-butyl acrylate) and B (e.g. n-butyl acetate) by rectification into essentially pure A and into essentially pure B, for example, only a separation into essentially pure A (n-butyl acrylate) and into a mixture of B (n-butyl acetate) and A (n-butyl acrylate) is performed.

The disadvantage of such an unsharp separation by rectification is evident: a part of the product desired in essentially pure form is lost as a component of the mixture, i.e. the yield of desired product is reduced.

At the same time, a shift in the acetic acid separation from the (meth)acrylic acid level to the alkyl (meth)acrylate level would be desirable insofar as (meth)acrylic acid is a substantially more readily polymerizable monomer than the corresponding alkyl ester, which is why the high temperatures required have a particularly disadvantageous effect on a separation by rectification with a high separation efficiency at the (meth)acrylic acid level. Separation of acetic acid by crystallization at the (meth)acrylic acid level is therefore often thought to be necessary for solving the problem. The disadvantage of this solution is however that it requires investment in a crystallization unit.

It is an object of the present invention to provide a process for the continuous preparation of alkyl esters of (meth)acrylic acid by reacting (meth)acrylic acid with alkanols of 1 to 8 carbon atoms in a solvent-free phase, in which, on the one hand, acetic acid-containing crude (meth)acrylic acid can still be used as a starting material and, on the other hand, a substantially alkyl acetate-free alkyl (meth)acrylate is obtained with a limited separation efficiency and without substantial loss of desired product.

We have found that this object is achieved by a process for the continuous preparation of alkyl esters of (meth)acrylic acid by reacting (meth)acrylic acid with alkanols of 1 to 8 carbon atoms in a solvent-free phase at elevated temperatures and in the presence of an acidic esterification catalyst, in which the (meth)acrylic acid, the alkanol and the acid catalyst are fed to a reaction zone, the resulting water as part of a mixture comprising starting alkanol is removed from the reaction mixture by rectification, during the residence time in the reaction zone, in a rectification unit I mounted on the reaction zone, the distillate obtained is separated into an organic phase containing starting alkanol and into a water-containing aqueous phase, the organic phase is recycled to the rectification unit I, the reaction mixture containing the desired ester is passed from the reaction zone into a separation zone comprising further rectification units and the resulting alkyl ester of (meth) acrylic acid is isolated in said separation zone, wherein the (meth)acrylic acid used is an acetic acid-containing crude (meth)acrylic acid, the acidic esterification catalyst is separated from the reaction mixture containing the desired ester before said reaction mixture is passed on into the separation zone comprising further rectification units, the residual reaction mixture I is fed to a rectification unit II and is separated therein by rectification into a low-boiler product containing desired ester and components boiling at a lower temperature than the desired ester and into a residual reaction mixture II comprising the desired ester and components boiling at higher temperature than the desired ester, at least the organic fraction of the low-boiler product not used as reflux to the rectification unit II is recycled from the rectification unit II into the reaction zone, the residual reaction mixture II is fed to a rectification unit III and the desired ester is separated therein from the components boiling at a higher temperature than the desired ester, the separation efficiency chosen in the rectification unit I is such that the distillate separated off by rectification and comprising water and starting alkanol also contains a portion of the alkyl acetate formed in the reaction zone as a byproduct and only a portion of the organic phase separated from the distillate obtained in the rectification unit I is recycled to the rectification unit I and the remaining amount is separated off as an alkyl acetate purge.

The novel process is preferably used for esterifying $C_4$- to $C_8$-alkanols with (meth)acrylic acid. This applies in particular to the preparation of the corresponding acrylates.

DE-A 19604253 discloses a process for the continuous preparation of alkyl esters of (meth)acrylic acid by reacting (meth)acrylic acid and alkanols of 1 to 8 carbon atoms in homogeneous, liquid, solvent-free phase at elevated temperatures and in the presence of an acidic esterification catalyst, in which the (meth)acrylic acid, the alkanol and the acid catalyst are fed to a reaction zone, the resulting water as part of a mixture comprising starting alkanol is separated off by rectification, during a residence time, in a rectification unit A) mounted on the reaction zone, the distillate obtained is separated into an organic phase containing starting alkanol and into a water-containing aqueous phase, the organic phase is recycled essentially completely to the rectification unit A), the reaction mixture is discharged from the reaction zone and is passed into a distillative separation zone comprising further rectification units and the resulting alkyl ester of (meth)acrylic acid is isolated therein, wherein essentially a part of the aqueous phase obtained in the rectification unit A) is recycled to the rectification unit A), the reaction mixture discharged from the reaction zone is fed to a rectification unit B and is separated therein into a product B containing the acidic esterification catalyst and into a product C containing the alkyl ester of (meth)acrylic acid, remaining starting alkanol and remaining (meth)acrylic acid, the product C is fed to the rectification unit C and the alkyl ester of (meth)acrylic acid is separated therein from the remaining starting alkanol and from the remaining (meth) acrylic acid, and the remaining starting alkanol and the remaining (meth)acrylic acid are recycled to the reaction zone. The disadvantage of the esterification method of DE-A 19604253 is that it is designed for esterifying a (meth) acrylic acid free of acetic acid.

DE-A 19604252 discloses an esterification process which essentially corresponds to that of DE-A 19604253. Although DE-A 19604252 includes the possibility of an acetic acid-containing (meth)acrylic acid as a starting compound, it envisages only the use of two additional separation columns as a measure for separating off alkyl acetate (column 9, lines 18–22).

The reason for the advantageousness of the novel procedure is that, on the one hand, the alkyl acetate purge with the organic phase of the low-boiler mixture separated off continuously in the rectification unit I from the esterification mixture and comprising starting alkanol and water is shifted to a point where an unsharp separation by rectification can be permitted without major loss of desired product. The reason for this is that an essentially alkyl acetate-free reaction mixture containing the desired ester is not strived for as early as in the reaction zone on which the rectification unit I is mounted, i.e. the removal of the alkyl acetate by rectification via the rectification unit I can be carried out with only low separation efficiency so that alkyl acetate still remains in the reaction mixture. This permits, via the rectification unit I, separation of a distillate which is comparatively low in alkyl (meth)acrylate and at the same time comparatively rich in alkyl acetate. Desired product significantly contained in the distillate is at most starting alkanol, which is of less value than the desired ester and, if required, can be extracted in a simple manner, for example, by means of water, from the discharged organic phase before it is disposed of (for example by incineration).

On the other hand, the novel process permits an essentially quantitative separation of the lower-boiling alkyl acetate from higher-boiling alkyl (meth)acrylate by rectification in the rectification unit II in a further "singly unsharp" separation by rectification (i.e. likewise requiring only a low separation efficiency), without there being any loss at all of desired product at this point as the distillate separated off in the rectification unit II and, as a result of the unsharpness of the separation, also containing desired ester is completely recycled to the reaction zone.

The novel process is particularly suitable for the direct esterification of a crude (meth)acrylic acid which contains up to 5% by weight, based on its weight, of acetic acid, i.e. it is particularly suitable for esterifying a (meth)acrylic acid which was produced by the catalytic gas-phase oxidation of the $C_3$-/$C_4$-precursors stated at the outset with molecular oxygen. In addition to acetic acid, the crude (meth)acrylic acid thus obtained will frequently also contain maleic acid and/or the anhydride thereof (together frequently up to 1% by weight, based on the weight of the crude (meth)acrylic acid) and low molecular weight aldehydes (frequently up to 0.5% by weight, based on the weight of the crude (meth) acrylic acid) and up to 0.5% by weight of other components (including polymerization inhibitors, e.g. phenothiazine). Other components may be, for example, propionic acid and diacrylic acid. The (meth)acrylic acid content, having the same basis as above, will as a rule be $\geq 93\%$ by weight. The advantages of the novel process are evident even when the crude (meth)acrylic acid contains from 0.01 to 0.05% by weight of acetic acid. Frequently, the acetic acid content of the crude (meth)acrylic acid will be from 0.1 to 3% by weight or from 0.2 to 1% by weight. At the same time, the maleic acid/maleic hydride content may be from 0.05 to 0.5% by weight.

The content of low molecular weight aldehydes in the crude (meth)acrylic acid which may be used according to the invention can frequently be from 0.02 to 0.1% by weight. Often, the (meth)acrylic acid content of the crude (meth) acrylic acid which may be used according to the invention is $\geq 95\%$ by weight, in many cases $\geq 97$ or $\geq 98$ or $\geq 99\%$ by weight. In principle, the novel process is suitable for the preparation of both acrylates and methacrylates of all $C_1$- to $C_8$-alkanols, among which methanol, ethanol, 2-ethylhexanol and n-butanol are noteworthy. The novel process is particularly suitable for the preparation of n-butyl acrylate.

Suitable acidic esterification catalysts for the novel process are both acidic ion exchange resins and strong mineral acids, e.g. sulfuric acid, or organic sulfonic acids, such as methanesulfonic acid, benzenesulfonic acid, dodecanesulfonic acid or para-toluenesulfonic acid, or a mixture of some or all of the abovementioned acids. Sulfuric acid is particularly suitable for carrying out the novel process. This applies in particular to the preparation of n-butyl acrylate.

The term rectification unit is to be understood here as well as below as a general term for apparatuses in which vapors produced by supplying heat rise and are in contact with downward-flowing liquid phase. As a rule, these are rectification columns which contain baffles for ensuring intimate contact between liquid and vapor. Such baffles are trays such as bubble trays, perforated trays, in particular dual-flow trays, and beds, packings and the like.

For easier comprehension of the relationships, the various rectification units are denoted by roman numerals. The various products described in detail also carry such a designation.

According to the invention, the reaction zone may consist of one or more reaction regions.

In one embodiment of the invention comprising a plurality of reaction regions, it is advantageous to cascade said regions. The liquid discharge stream of a reaction region expediently forms the feed of the downstream reaction region. This can be effected in a simple manner with the aid of an overflow or by means of pumps. Where the individual reaction regions are apparatuses separated from one another, the number thereof is expediently $\geq 2$ and $\leq 4$, taking into account the capital costs. If more than one reaction region is provided within one and the same reactor (for example by the use of baffles), the number of reaction regions may also be greater than 4. In the case of a plurality of reaction regions, the vapors of the individual reaction regions can be fed to a common rectification unit, for example a common rectification column, whose liquid discharge is expediently fed to the first reaction region. According to the invention, however, it may be useful to mount one rectification unit each on a plurality of reaction regions, if required, all reaction regions, and recycle their liquid reflux to one or more reaction regions, expediently to those on which the rectification units are mounted. Frequently, no rectification unit is mounted on the first reaction region.

Since the acidic esterification catalysts to be used according to the invention are generally relatively sparingly volatile, and owing to the removal of the water of esterification from the reaction zone via the rectification unit I, the amount, based on the amount of reaction mixture contained in the respective reaction region, of acidic esterification catalyst contained in successive reaction regions usually increases from reaction region to reaction region in the novel process.

As a rule, the novel esterification in the reaction zone is operated at reduced pressure (i.e. <1 bar), which facilitates the removal of the water of reaction by rectification via the rectification unit I. However, it may also be carried out at atmospheric pressure (i.e. at 1 bar) or at superatmospheric pressure. Usually, the reaction zone with the mounted rectification unit I is separated both spatially and in terms of regulation from the other rectification units. The conditions in the reaction region and in the rectification units used for separating off the desired ester can therefore be established in a very flexible manner. Usually, the reaction pressure in the reaction regions is from 100 mbar to $\leq 1$ bar, frequently from 100 mbar to 800 mbar, in many cases from 500 to 700 mbar.

The temperature of the reaction mixture in the reaction regions usually corresponds to the pressure set and to the composition of the reaction mixture present in the reaction region, i.e., in the case of cascading (in the case of a plurality of reaction regions), the reaction temperature generally increases along the cascade (the reaction pressure is usually kept constant along the cascade).

Particularly if a starting alkanol of 4 to 8 carbon atoms, e.g. n-butanol, is used for the novel process, the temperature in the reaction zone is from 70 to 160° C. It is usually from 70 to 150° C., preferably from 80 to 130° C., in the first reaction region and from 100 to 160° C., preferably from 110 to 130° C., in the last reaction region. In the case of n-butanol, it is expedient to choose the reaction temperature in all regions within from $\geq 100°$ C. to $\leq 140°$ C. i.e. to allow the reaction temperature to increase from $\geq 100°$ C. in the first reaction region to $\leq 140°$ C. in the last reaction region.

The total residence time of the reactants in the reaction regions is as a rule from 0.25 to 15 h, frequently from 1 to 7 h, or from 2 to 5 h. The residence time of the reactants usually decreases in successive reaction regions.

The content of acidic esterification catalyst in the reaction zone is expediently from 0.1 to 20, frequently from 0.5 to 5, % by weight, based on the reaction mixture contained therein, of $H_2SO_4$ or of an equivalent (usually equimolar) amount of organic sulfonic acid and/or sulfuric acid and/or acidic, e.g. sulfonic acid, ion exchange resin.

According to the invention, the distillate obtained in the rectification unit I, usually at the top of a rectification column, is as a rule (especially in the case of an esterification of $C \geq_4$-alkanols) separated into an organic and into an aqueous phase by cooling during condensation (alternatively, phase separation by rectification is also suitable). The organic phase predominantly comprises organic components (mainly alkanol, alkyl acetate, alkyl (meth)acrylate and dialkyl ether) while the aqueous phase predominantly comprises water of esterification. As a rule, in particular in the preparation of n-butyl acrylate, none of the aqueous phase is recycled to the rectification unit I. This is usually separated off instead. If required, the alkanol present in solution in small amounts in the aqueous phase can be separated off by stripping in an alkanol stripping column, for example by means of steam or air, and can be recycled to the reaction zone, usually to the first reaction region. Recycling of a part of the aqueous phase to the rectification unit I is usually practised only when the distillate separated off in the rectification unit I could contain (meth)acrylic acid (in significant amounts) without such recycling. The amount of organic phase recycled to the rectification unit I is as a rule such that the reflux ratio (the ratio of amount recycled to amount removed) is from 5 to 40, preferably from 10 to 30. In general, the separation efficiency in the rectification unit I is frequently chosen so that the alkyl acetate content of the organic phase removed is at least 5, as a rule at least 10, in many cases at least 20, % by weight.

Before the organic phase which contains alkyl acetate and is removed is disposed of, for example incinerated, it can be subjected to extraction with water to separate off alkanol contained therein, e.g. n-butanol, into the aqueous phase, in order to increase the yield. The aqueous phase containing alkanol, e.g. n-butanol, can likewise be fed to the abovementioned alkanol stripping column and in this way the alkanol separated off therein can be recycled to the reaction zone. The water freed from alkanol in the alkanol stripping column can be disposed of as waste water requiring treatment and/or reused for the extraction.

Alternatively, the alkyl acetate-containing organic phase removed could also be worked up by rectification to give a top product comprising mainly alkyl acetate and alkanol and a bottom mixture comprising mainly alkyl (meth)acrylate and alkanol. The bottom mixture could be recycled directly to the reaction zone and the top product either thermally utilized or worked up as follows:

Extraction of the alkanol with water and recovery by stripping, for example with steam, or rectification and recycling of the alkanol to the reaction zone;

Hydrolysis with aqueous alkali solution and subsequent separation of the alkanol from the aqueous phase by stripping or rectification and recycling of the alkanol to the reaction zone;

The above hydrolysis could also be carried out directly with the alkyl acetate-containing purge stream.

In the case of esterification of 2-ethylhexanol, the alkyl acetate-containing organic phase removed is expediently simultaneously the purge for octene formed as a byproduct (dehydration of 2-ethylhexanol).

As a rule, both the (meth)acrylic acid (usually stabilized with 200 to 1000 ppm by weight of polymerization inhibitor (as a rule phenothiazine)) and the acid esterification catalyst are fed directly to the reaction zone (spatially separately and/or in combination). The starting alkanol to be esterified is preferably fed to the reaction zone via the rectification unit I mounted on said zone. However, the starting alkanol could of course also be fed directly to the reaction zone.

The rectification unit I may consist of one or more rectification columns of known design, for example having bubble trays or sieve trays. Usually, this is supplemented by associated condensers and separation vessels. The reaction regions may consist of, for example, reactors having natural-circulation or forced-circulation evaporators, i.e. the reaction mixture can be mixed by stirring, circulation by means of a pump and/or natural circulation. Heat is supplied in a manner known per se, for example by a double-jacket heater or external and/or internal heat exchangers.

To stabilize the rectification unit I to prevent undesired formation of polymer initiated by free radicals, a solution of a polymerization inhibitor is expediently applied to the top of said unit. A suitable solvent in this respect is, for example, the alkyl (meth)acrylate intended as the desired product or the organic phase of the distillate separated off in the rectification unit II, which organic phase is to be recycled to the rectification unit I. A preferably used polymerization inhibitor is phenothiazine.

The condensers (for example, plate-type or tube-bundle condensers) in which the vapors ascending in the rectification unit are condensed to obtain the distillate to be separated off in the rectification unit I are expediently likewise stabilized by means of polymerization inhibitors known per se. An aqueous solution (about 0.1–1% strength by weight) of at least one inhibitor (as a rule having at least a water solubility of 1% by weight (25° C., 1 bar)) is advantageously applied to the condenser and/or added to the condensate for this purpose. Suitable water-soluble inhibitors of this type are, for example, hydroquinone, p-nitrosophenol, phenyldiamines, such as Kerobit BPD (N,N'-diisobutyl-p-phenylenediamine), nitrosodiethylaniline, 2,2,6,6-tetramethylpiperidine-N-oxyl, 4-hydroxy-2,2,6,6-tetramethylpiperidine-N-oxyl or mixtures of the abovementioned members. An aqueous solution which contains 4-hydroxy-2,2,6,6-tetramethylpiperidine-N-oxyl (preferably as the sole inhibitor) is preferably used, in particular in the case of the preparation of n-butyl acrylate.

Before the discharge from the reaction zone, which as a rule essentially comprises desired ester, unreacted (meth)acrylic acid, byproducts which are lower-boiling than the desired ester, such as alkyl acetate or dialkyl ether, acidic esterification catalyst, higher-boiling oxyesters formed by Michael addition and polymerization inhibitor, is fed to the rectification unit II, according to the invention the acidic esterification catalyst is separated from the reactor discharge.

In detail, this can be effected in various ways.

In the case of strong mineral acids, e.g. sulfuric acid, and/or organic sulfonic acids, the separation can be carried out in a particularly simple manner known per se, for example by washing the esterification discharge with water. The resulting aqueous phase containing the acidic esterification catalyst and unreacted (meth)acrylic acid and any process polymerization inhibitor can expediently be recycled directly to the reaction zone, disposed of and/or combined with the alkaline aqueous phase mentioned in the next section, for the purpose of back-extraction. The demand for fresh acidic esterification catalyst is reduced as a result of circulation. In a further wash stage, the abovementioned separation can be completed by subsequent washing of the remaining organic phase with an aqueous alkali (preferably sodium hydroxide and/or potassium hydroxide) solution.

The alkaline aqueous phase obtained can be disposed of or subsequently acidifed, for example with sulfuric acid, and (meth)acrylic acid contained therein can be back-extracted by means of a mixture of alkanol and alkyl (meth)acrylate (cf. DE-A 2 323 328) and the organic phase can be recycled to the reaction zone to increase the yield. The aqueous phase which takes up a certain amount of alkanol will be expediently be fed to the alkanol stripping column.

According to the invention, the residual reaction mixture I thus remaining is fed to a rectification unit II (usually to the upper half) and is separated therein into a residual reaction mixture II comprising mainly the desired ester and byproducts having a higher boiling point than the desired ester (for example the oxyesters) and low-boiler product comprising a mixture of byproducts having lower boiling points than the desired ester (residual amounts of water, alkanol, alkyl acetate, dialkyl ether) and desired ester.

The rectification unit II may consist, for example, of a heat exchanger of conventional design, for example an external tube-bundle heat exchanger, and a rectification column having conventional baffles, for example dual-flow trays, sieve trays, beds or stacked packings, and may be supplemented by a condenser for the vapors of the low-boiler product, for example a plate-type or tube-bundle condenser. As a rule, this is also connected to a phase separation vessel in which (especially in the case of esterifications of $C \geq_4$-alkanols) the condensed low-boiler product is separated into a residual water phase and an organic phase (alternatively, the phase separation may also be effected by rectification, depending on the chain length of the alkanol). Preferably, the residual water phase is separated off and is fed to the alkanol stripping column mentioned repeatedly above. A part of the organic phase of the low-boiler product is recycled as a reflux, (reflux ratio is as a rule from 3 to 20, frequently from 5 to 10) to the rectification unit II and that part of the organic phase of the low-boiler product which is not used as reflux is recycled to the reaction zone (for example via the rectification unit mounted on the first reaction region; in the case of a rectification column, expediently into its lower third). However, the abovementioned phase separation can in principle also be omitted. In this case, a part of the low-boiler product which has not been subjected to phase separation is used as reflux and the other part is recycled to the reaction zone.

If the organic phase of the low-boiler product is recycled to the reaction zone, it is expedient not to recycle this total amount directly to the reaction zone. Rather, a portion thereof, if necessary with the addition of a small amount of alkanol (frequently from 10 to 60% by weight, based on the mixture formed after the addition; as a rule so that the total amount of alkanol in the mixture is at least 30, frequently from 30 to 60, % by weight), can be used for the back-extraction of (meth)acrylic acid from the wash water acidified (as a rule to $pH \leq 2$) with, for example, sulfuric acid (preferably as a 60% strength by weight aqueous solution) and resulting from the alkali wash of the discharge from the reaction zone and only the organic phase obtained thereby can be recycled to the reaction zone (preferably via the mounted rectification unit I; in the case of a column, expediently in the lower third). Another part of the organic phase of the low-boiler product can be used for the preparation of a phenothiazine solution and this can be recycled to the reaction zone via the top of the rectification unit I, thus stabilizing the rectification unit I. For the stabilization of the rectification unit II, some of the abovementioned phenothiazine solution can also be recycled as a reflux to the rectification unit II, preferably to the top thereof.

The condenser belonging to the rectification unit II is as a rule likewise operated with stabilization to prevent polymerization. Preferably, a solution of one or more of the following polymerization inhibitors selected from the group consisting of thiodiphenylamines (e.g. phenothiazine), nitroso compounds (e.g. p-nitrosophenol), nitroxyl compounds (e.g. 2,2,6,6-tetramethylpiperidine-N-oxyl) and phenylenediamines (e.g. N,N'-diisobutyl-p-phenyldiamine= Kerobit BPD) is applied to the condenser surface and/or added to the condensate as a stabilizer solution for this purpose. Desired ester or organic phase of the low-boiler product is expediently used as solvent.

As a rule, the residual reaction mixture II is removed as bottom product from rectification unit II and fed to a further rectification unit III (usually into the lower half of a conventional rectification column). In this, the desired ester can be separated off as top product in high purity and essentially free of alkyl acetates. The associated condenser is preferably likewise operated with stabilization to prevent polymerization. An advantageous polymerization inhibitor at this point is a solution of hydroquinone monoethyl ether (HQME) in desired ester. In this way, the desired product can be obtained in a form containing 10–20 ppm by weight of HQME as storage stabilizer. A part of the product thus stabilized is recycled as reflux (frequently at a reflux ratio of from 0.1 to 5 or from 0.3 to 1) to the rectification unit III. Moreover, it is expedient to stabilize the rectification unit III additionally by means of an about 0.01 to 2% strength by weight solution of HQME in desired ester. Where a rectification column is used as rectification unit III, the reflux stabilized with HQME (as a rule with from 10 to 20 ppm by weight thereof) is as a rule recycled at the top of the column and the additional 0.01 to 2% strength by weight HQME solution in desired ester is added at a column tray of the upper column half, above the feed of the residual reaction mixture II.

The abovementioned alkanol stripping of the waste waters obtained at various points in the process described above can be carried out, for example, in a heatable stirred reactor having an attached column or by the countercurrent principle in a stripping column. The energy can be supplied in a manner known per se (for example double-jacket coiled tube heater, circulation heater, etc.). The alkanol-containing waste water can be fed in, for example, at the top of the column and stripped by the countercurrent method with steam (from 0.1 to 10 $t/m^3$, temperature, for example, 103° C., pressure, for example, 4 bar). The condensate separates, in particular in the case of $C \geq_4$-alkanols, into an aqueous phase and into an alkanol phase, of which the latter can be either recycled directly to the reaction zone or concomitantly used in the back-extraction of a (meth)acrylic acid from the wash waters, for example of the alkali wash. The alkanol stripping described above can, if required, also be replaced by a simple separation by rectification.

The operating conditions of the rectification units II and III are typically:

Rectification unit II:
top temperature: from 70 to 90° C.;
top pressure: from 150 to 190 mbar;
bottom temperature: from 100 to 120° C.;
bottom pressure: from 250 to 350 mbar.

Rectification unit III:
top temperature: from 70 to 90° C.;
top pressure: from 90 to 120 mbar;
bottom temperature: from 100 to 120° C;
bottom pressure: from 150 to 180 mbar.

The high-boiling residue (bottom product) remaining in the rectification unit III, essentially still containing desired ester and composed of oxyester, polymerization inhibitor and alkyl (meth)acrylates oligomerized and/or polymerized by means of free radicals can, in order to increase the yield further, advantageously be subjected to a process for cleavage of the Michael oxyester, as described in DE-A 19 701 737, DE-A 19 536 191, DE-A 19 536 184, DE-A 19 547 485, DE-A 19 547 459 or CN-A 1 063 678 and the resulting cleavage products can be recycled directly to the reaction zone. The high-boiling residue remaining in the cleavage is finally disposed of, for example incinerated.

Oxyesters as typical byproducts of acid-catalyzed esterifications of (meth)acrylic acid are formed, for example, if unreacted starting alkanol undergoes an addition reaction at the ethylenically unsaturated double bond of already formed alkyl (meth)acrylate with formation of a compound of the formula I shown below and unreacted meth(acrylic) acid undergoes said addition reaction with- formation of a compound of the formula II (Michael addition). Gradual multiple addition is also possible. Mixed types may also occur. These adducts (alkoxy ester and acyloxy ester) are referred to as oxyesters for short:

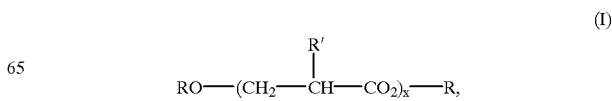

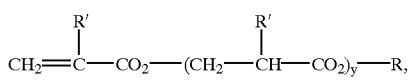

where
- x,y are each, for example, an integer from 1 to 5;
- R is alkyl and
- R' is H or CH$_3$.

The problem of oxyester formation is particularly pronounced in the preparation of esters of acrylic acid, the oxyesters mainly formed being the alkoxypropionic ester and the acyloxypropionic ester where x and y are each 1. The formation of oxyesters is described, inter alia, in DE-A 2 339 529 and U.S. Pat. No. 5,734,075. Of particular importance is the oxyester formation in the preparation of (meth) acrylates of C$_1$- to C$_8$-alkanols, in particular C$_4$- to C$_8$-alkanols, very particularly in the preparation of n-butyl acrylate and 2-ethylhexyl acrylate. It is typical of the oxyesters that their boiling point is above the boiling points of starting acid, starting alkanol and desired ester formed.

It is essential that the oxyester formation is reversible, i.e. the oxyesters can be cleaved back into their starting compounds by the action of elevated temperatures in the presence of acidic cleavage catalysts.

Below, it is also important that (meth)acrylic acid can undergo a Michael addition reaction reversibly with itself. The resulting oligomers of (meth)acrylic acid are to be referred to below as Michael oligomers to distinguish them from oligomers formed by free radical polymerization. (Meth)acrylic acid in the form of Michael oligomers is obtained as a bottom product, for example in the distillative treatment of crude (meth)acrylic acid (cf. for example DE-A 2 235 326).

(Meth)acrylic acid in the form of Michael oligomers can be characterized by the formula (III)

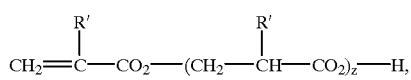

where
- z is an integer $\geq 1$, frequently from 1 to 5,
- and R' is H or CH$_3$.

Suitable oxyester cleavage catalysts are, for example, mineral acids such as sulfuric acid, or phosphoric acid, and organic acids, such as methanesulfonic acid or p-toluenesulfonic acid.

The cleavage of the oxyesters contained in the bottom product of the rectification unit III is therefore possible in a simple manner by adding at least one acidic cleavage catalyst to the bottom product and then keeping the mixture at elevated temperatures, as a rule from 140 to 260° C., frequently from 180 to 230° C. The cleavage is preferably carried out at atmospheric pressure or at reduced pressure (<1 bar), typically at from 500 to 700 mbar, so that the cleavage products vaporize immediately and can be recycled directly to the reaction zone (for example via the rectification unit I mounted on the reaction zone), if necessary after condensation and stabilization with polymerization inhibitors. As a rule, the cleavage according to the invention is carried out in the presence of a total amount of from 1 to 50, preferably from 1 to 40 or from 5 to 20, % by weight, based on the amount of the oxyesters to be cleaved, of acidic cleavage catalysts.

According to the invention, it is advantageous if the cleavage is carried out in the presence of an acidic cleavage catalyst of the formula IV

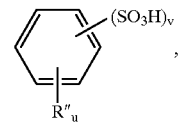

where
- R", independently of one another, are each alkyl radicals of six to twenty carbon atoms,
- u is an integer from 1 to 3 and
- v is 1 or 2.

The abovementioned sulfonic acids of the formula (IV) are disclosed, for example, in EP-A 521 488. u may be 1 or 2 or 3 and v may simultaneously be 1 or 2. Frequently, the radicals R" are alkyl radicals of 8 to 16 or 10 to 14 carbon atoms. Suitable typical compounds (IV) are accordingly, for example, octylbenzenesulfonic acids, such as n-octylbenzenesulfonic acid, nonylbenzenesulfonic acids, such as n-nonylbenzenesulfonic acid, decylbenzenesulfonic acid, such as n-decylbenzenesulfonic acid, undecylbenzenesulfonic acids, such as n-undecylbenzenesulfonic acid, dodecylbenzenesulfonic acids, such as n-dodecylbenzenesulfonic acid, tridecylbenzenesulfonic acids, such as n-tridecylbenzenesulfonic acid, tetradecylbenzenesulfonic acids, such as n-tetradecylbenzenesulfonic acid, pentadecylbenzenesulfonic acids, such as n-pentadecylbenzenesulfonic acid, hexadecylbenzenesulfonic acids, such as n-hexadecylbenzenesulfonic acid, heptadecylbenzenesulfonic acids, such as n-heptadecylbenzenesulfonic acid, octadecylbenzenesulfonic acids, such as n-octadecylbenzenesulfonic acid, nonyldecylbenzenesulfonic acids, such as n-nonyldecylbenzenesulfonic acid, heptadecylbenzenesulfonic acids, such as n-heptadecylbenzenesulfonic acid, octadecylbenzenesulfonic acids, such as n-octadecylbenzenesulfonic acid, nonyldecylbenzenesulfonic acids, such as n-nonyldecylbenzenesulfonic acid, and eicosylbenzenesulfonic acids, such as n-eicosylbenzenesulfonic acid. According to the invention, mixtures of compounds (IV) can of course also be used. Such mixtures are employed, as a rule, when compounds (IV) which are merely of industrial purity are used. Examples of such industrial, commercially available compounds (IV) are the alkyl benzenesulfonic acids Bio-Soft® S-100 (average molecular weight about 318, average R" chain length 11.5 carbon atoms, manufacturer Stepan Co.), AAS-985 (linear alkylbenzenesulfonic acid having an average alkyl chain length of $C_{11-C12}$, manufacturer Continental Chemical Co.), Vista SA 697 and Vista SA 597 (linear alkylbenzenesulfonic acids having an average molecular weight of 342 and 318, respectively, manufacturer Vista Chemical Co.), Stepantan® H-100 (a branched dodecylbenzenesulfonic acid, manufacturer Stepan Co.) and a technical-grade alkylbenzenesulfonic acid from Alfa Products Co., in which R" comprises 1% by weight of $C_{10}$, 40% by weight of $C_{11}$, 28% by weight of $C_{12}$ and 31% by weight of $C_{13}$.

In the novel process, the sulfonic acids (IV) can be used both as sole acidic cleavage catalysts and as a mixture with other acidic cleavage catalysts, for example sulfuric acid, phosphoric acid, methanesulfonic acid and/or p-toluenesulfonic acid, i.e. the molar fraction of the novel compounds (IV) may be, for example, ≧1 mol %, ≧5 mol %, 10 mol %, ≧15 mol %, ≧25 mol %, ≧50 mol %, ≧75 mol %, ≧90 mol %, ≧95 mol % or 100 mol %, based on the total amount of acidic cleavage catalysts used in the novel process. Preferably, the abovementioned fraction of the novel compounds (IV) is at least 25, particularly preferably at least 50, very particularly preferably at least 75, particularly advantageously 100, mol %. The presence of novel compounds (IV) has an advantageous effect on the cleavage in that, in their presence, the cleavage residue obtained is generally less viscous and usually does not contain solids.

Moreover, the novel cleavage can be carried out according to DE-A 19 547 459 or DE-A 19 547 485, additionally in the presence of monomeric (meth)acrylic acid and/or (meth)acrylic acid in the form of Michael oligomers. The amount of such monomeric (meth)acrylic acid and/or (meth) acrylic acid in the form of Michael oligomers may be up to 50% by weight or more, based on the amount of oxyesters to be cleaved. Frequently, the abovementioned amount of monomeric and/or oligomeric (meth)acrylic acid is from 5 to 50 or from 10 to 40 or from 15 to 30% by weight.

The monomeric and/or oligomeric (meth)acrylic acid is usually added in a form known per se and stabilized by means of polymerization inhibitors to the bottom product to be subjected to the cleavage. The bottom product obtained in the distillative purification of crude (meth)acrylic acid and containing mainly compounds of the formula (III) can be used in a particularly simple manner as oligomeric (meth) acrylic acid (cf. for example DE-A 22 35 326). The presence of monomeric (meth)acrylic acid and/or (meth)acrylic acid in the form of Michael oligomers in the novel cleavage results in particular in a higher cleavage rate and reduced formation of ether and olefin byproducts.

In addition, according to DE-A 19 701 737, the novel cleavage of the bottom product can be carried out in the presence of water. The abovementioned amount of water is as a rule from 0.1 to 20, frequently from 1 to 10% by weight, based on the amount of the oxyesters to be cleaved.

The bottom product to be cleaved and the compounds (IV) preferably to be used and any other acidic cleavage catalysts likewise to be added and monomeric (meth)acrylic acid and/or (meth)acrylic acid in the form of Michael oligomers and, if required, water can be added to the bottom product to be cleaved before it is transferred to the cleavage reactor. However, they may also be added separately to the cleavage reactor. A part or the total amount of the acidic cleavage catalysts required according to the invention may also be the acidic esterification catalysts. According to an advantageous embodiment of the invention, the novel cleavage is carried out in the presence of molecular oxygen.

It is particularly advantageous if a stripping gas, which preferably contains molecular oxygen, is passed through the mixture to be cleaved in the novel process as an entraining agent for the cleavage products. Air or a mixture of air with inert gas (e.g. nitrogen) is expediently used as stripping gas.

If a stripping gas is passed through the cleavage mixture during the cleavage, the amount thereof is usually 1–100 l/h×1. As a rule, the cleavage will require reaction times of from 1 to 15 h. The conversion of the cleavage is usually ≧90% by weight.

For example, a single heatable stirred reactor having double-jacket heating or heating coil or a forced-circulation evaporator, for example a falling-film evaporator or flash evaporator, coupled with a dwell tank, may be used for carrying out the novel cleavage. For better separation of the cleavage products from the bottom product, a rectification apparatus, for example a packed column or tray column, mounted on the cleavage apparatus may be expedient. This rectification apparatus is as a rule operated with stabilization by means of polymerization inhibitors (e.g. phenothiazine, hydroquinone monomethyl ether, hydroquinone, etc.). Of course, the bottom product to be cleaved and originating from the esterification is also stabilized by means of polymerization inhibitors to prevent polymerization.

The novel cleavage reaction takes place, for example, by a method in which the bottom product to be cleaved is removed continuously from the rectification unit III and fed with the required cleavage catalysts, any monomeric (meth) acrylic acid and/or (meth)acrylic acid in the form of Michael oligomers and, if required, water to the cleavage reactor. However, the reaction can also be carried out batchwise. It is also possible to carry out a semicontinuous reaction in which the bottom product to be cleaved and any additives added to said bottom product, are fed continuously to the cleavage reactor which contains the acidic cleavage catalyst, and the bottom product obtained during the cleavage is removed batchwise from the cleavage reactor only after the end of the cleavage.

The cleavage products (alkanol, alkyl (meth)acrylate and (meth)acrylic acid) formed in the novel cleavage are usually separated off continuously in vapor form and, in contrast to the process of U.S. Pat. No. 5,734,075, can be recycled directly to the reaction zone, as a rule after their condensation (the corresponding condenser is preferably stabilized with phenothiazine), without intermediate purification. However, the recycling could of course also be carried out according to U.S. Pat. No. 5,734,075.

Preferably, the cleavage products are recycled to the reaction zone via the rectification unit I (recycling is expediently effected into the lower half of the rectification column).

Of course, the novel cleavage process can also be carried out in a plurality of stages (for example in a cascade, e.g. as in CN-A 1063678).

Preferably, the novel cleavage is carried out in two stages, the content of acidic cleavage catalysts being brought to, as a rule, from 1 to 20% by weight in the first cleavage stage and to from 5 to 40% by weight in the second stage, based on the contained amount of oxyesters to be cleaved. The residence time in the individual stages may be identical or different. Preferably, it increases from the first to the last stage. In a two-stage procedure, the residence time of the cleavage mixture in the first stage is expediently from 1 to 15 h and that in the second stage from 10 to 40 h.

Furthermore, in a multistage procedure, the cleavage temperature preferably increases toward the final stage. In the two-stage case, the cleavage temperature in the first stage is expediently from 160 to 200° C. and that in the second stage is from 180 to 220° C.

The advantage of the stepwise cleavage described above is that the bottom product obtained in the esterification still contains, as a rule, significant amounts of the desired ester which, at the high cleavage temperatures, are particularly susceptible to (free radical) polymerization and also not inert with respect to the acidic cleavage catalysts. Under comparatively mild cleavage conditions in the first stage, these desired ester fractions can be isolated essentially unchanged with the resulting cleavage products in a gentle manner before the cleavage can be completed in the subsequent stages under more severe cleavage conditions. When a multistage cleavage is carried out continuously, the pressure in successive stages may be identical or different. In the case of a constant pressure, the transport from one stage to the other can be effected in a simple manner by level-controlled overflow. In the case of different pressures, transport of the mixture by pumping is advisable.

In a multistage cleavage, it is furthermore advantageous if the residue of the last cleavage stage is recycled at least partly (expediently from 10 to 80% of its weight) to the first cleavage stage.

Furthermore, different amounts of monomeric and/or oligomeric (meth)acrylic acid, of water and of acidic cleavage catalysts may be fed to the individual stages.

The use of the procedure described to date is particularly suitable in the case of a direct esterification of (meth)acrylic acid with $C_1$- to $C_8$-alkanols, e.g. n-butanol, in homogeneous, liquid, solvent-free phase, catalyzed by means of strong mineral acids, e.g. sulfuric acid.

However, it is also suitable in the case of corresponding direct esterifications under heterogeneous catalysis by means of acidic ion exchange resins. In this case, the separation of the esterification catalyst from the reactor discharge from the reaction zone can be carried out in a particularly simple manner by, for example, mechanical retention. The residual reaction mixture I obtainable in this manner can moreover be worked up in the manner described. (Meth)acrylic acid not converted in the reaction zone may in this case be obtained, for example, as part of the low-boiler product at the top of rectification unit II and can then be recycled as part of said product to the reaction zone.

Where organic sulfonic acids are used as acidic esterification catalysts, the separation of the acidic esterification catalyst from the reactor discharge of the reaction zone can be effected as described in the case of sulfuric acid, by washing with aqueous phase or by rectification, as described, for example, in DE-A 19604253 or DE-A 19604252, i.e. the desired ester and all components of the reactor discharge which have a lower boiling point than said ester are separated from the reactor discharge, for example via the top of a rectification column. The further working up of the residual reaction mixture I obtained in this manner via the top can be effected as described above. The further processing of the bottom product containing the acidic esterification catalyst and byproducts having a higher boiling point than the desired ester can be carried out in each case as described in DE-A 19604253 or DE-A 19604252.

The molar ratio of (meth)acrylic acid to alkanol in the reaction zone in the novel process is chosen to be, as a rule, from 0.5:1 to 2:1, preferably from 0.7:1 to 1.2:1. In the novel continuous procedure, the reactants are fed continuously to the reaction zone and the reaction discharge of the reaction zone is removed continuously. Acidic esterification catalyst which is not circulated is also continuously added to the reaction zone.

Suitable starting materials to be esterified in the novel process include alkanols and (meth)acrylic acids of the following purity:

a) Crude (meth)acrylic acid containing
  $\geq$95% by weight of (meth)acrylic acid,
  up to 5% by weight of acetic acid,
  up to 0.5% by weight of maleic acid/maleic anhydride,
  up to 0.5% by weight of aldehydes,
  from 250 to 550 ppm by weight of phenothiazine;

b) Crude n-butanol containing
  $\geq$95% by weight of n-butanol,
  up to 0.1% by weight of isobutanol,
  up to 0.1% by weight of di-n-butyl ether,
  up to 0.05% by weight of water,
  up to 0.05% by weight of butyraldehyde,
  up to 250 ppm by weight of butyl butyrate;

c) Crude 2-ethylhexanol containing
  $\geq$95% by weight of 2-ethylhexanol,
  up to 2500 ppm by weight of 2-ethyl-4-methylpentanol,
  up to to 400 ppm by weight of 2-ethylhexanal;

d) Crude methanol containing
  $\geq$99.8% of methanol,
  up to 0.1% by weight of water;

e) Crude ethanol containing
  $\geq$94% by weight of ethanol,
  up to 6% by weight of water,
  up to 0.1% by weight of acetic acid.

These can in principle also be used in the esterification processes of DE-A 19536178, DE-A 19604267, DE-A 19604253 and DE-A 19604252. Of course, (meth)acrylic acid free of acetic acid can also be used in the novel process.

The novel process is to be described in more detail below with reference to an exemplary esterification of n-butanol with acrylic acid.

EXAMPLES

Example 1

A stirred kettle cascade (reaction zone) comprising three stirred reactors, each of which had a reaction volume of 1 l and was equipped with a dual-flow rectification tray column (20 trays), which together formed a rectification unit I, a condenser and a phase separation vessel, was loaded continuously with, per hour, 539 g of crude acrylic acid, 15 g of a 98% strength by weight sulfuric acid, 605 g of n-butanol and 107 g of the organic fraction of the low-boiler product obtained in the rectification unit II. Loading was effected into the first stirred reactor. The crude acrylic acid had been produced by catalytic gas-phase oxidation of propene and subsequent working up of the reaction gas mixture and had the following composition:

99.3% by weight of acrylic acid,
  0.2% by weight of acetic acid,
  0.03% by weight of propionic acid,
  0.11% by weight of maleic anhydride,
  0.2% by weight of Michael diacrylic acid,
  0.1% by weight of phenothiazine and
  0.06% by weight of other byproducts from the production of crude acrylic acid.

The reaction temperatures in the three stirred reactors were 107° C., 118° C. and 125° C., increasing in the direction of the reaction path. The pressure in the three stirred reactors was uniformly 700 mbar.

The top product obtained in each case in the rectification tray columns of rectification unit I separated in each case into an organic phase and into an aqueous phase after its condensation in the phase separation vessels. The combined aqueous phases were removed and were disposed of. The major part of the organic phases was recycled via the top to the respective rectification tray column. The residual amounts were combined and their total amount (25 g/h), which comprised 24% by weight of n-butyl acrylate, 54% by weight of n-butanol, 8% by weight of n-butyl acetate, 2% by weight of dibutyl ether and 11% by weight of water, was removed and incinerated.

The rectification tray columns of rectification unit I were stabilized by adding in each case 30 g/h of 1% strength by weight solution of phenothiazine in pure n-butyl acrylate obtained as in the example (purity >99.9% by weight), at the uppermost tray.

The condensers were each stabilized by applying (to the cooling walls) 50 ml/h of a 0.1% strength by weight aqueous solution of 4-hydroxy-2,2,6,6-tetramethylpiperidine-N-oxyl.

1176 g/h of reactor discharge were removed continuously from that stirred reactor of the reaction zone which was operated at the highest reaction temperature. An analysis of the reactor discharge showed that the acrylic acid conversion was 98.7 mol % and was based on the amount of acrylic acid fed continuously to the reaction zone.

The reactor discharge was washed first with a 6% strength by weight aqueous sodium hydroxide solution (200 ml/h) and then with water (100 ml/h) in mixer-settler apparatuses. The resulting aqueous phases were combined and disposed of.

The resulting, essentially acid-free, organic phase was fed (at the 30th tray) to a rectification unit II which was formed by a rectification column having 40 bubble trays and which had been supplemented by a circulation evaporator, a condenser and a phase separation vessel, and said organic phase was separated, at a bottom temperature of 107° C., a top pressure of 175 mbar and a top temperature of 80° C., into a bottom product comprising mainly n-butyl acrylate and high boilers (boiling point>boiling point of n-butyl acrylate) and into a low-boiler product which was removed at the top of the column. In the phase separation vessel, the low-boiler product separated into an organic phase and into an aqueous phase. The aqueous phase was removed and disposed of. With a reflux ratio of 10, a part of the organic phase was recycled to the uppermost tray of the rectification column and the other part, 107 g/h, was recycled to the first stirred reactor of the reaction zone. The composition of the organic phase was 63.3% by weight of n-butyl acrylate, 1.3% by weight of n-butyl acetate, 26% by weight of n-butanol and 0.5% by weight of di-n-butyl ether.

The rectification unit II was stabilized by applying 50 g of 1% strength by weight solution of phenothiazine in pure n-butyl acrylate obtained as in the example.

The bottom product obtained in the rectification unit II was fed via the 10th tray to a rectification unit III formed by a dual-flow rectification tray column and supplemented by a circulation evaporator and a condenser, and n-butyl acrylate in a purity (including polymerization inhibitor) of >99.9% by weight (the butyl acetate content of the n-butyl acrylate obtained was less than 0.01% by weight) was isolated by the top of the dual-flow rectification tray column. Based on the amount of acrylic acid used, the n-butyl acrylate yield was 95% by weight. The dual-flow rectification tray column was operated at a bottom temperature of 110° C., and a top temperature of 80° C. and a top pressure of 105 mbar. The column was stabilized by means of a solution of HQME in desired ester (0.3% strength by weight) added to the condenser via the reflux (the reflux contained 15 ppm of HQME and the reflux ratio was 0.4) and by adding a 0.3% strength by weight HQME solution in desired ester at the 15th tray.

The bottom product obtained in the rectification unit III was removed continuously in an amount of 48 g/h. It still contained 14% by weight of n-butyl acrylate and otherwise comprised mainly butyl butoxy propionate (58% by weight) and butyl acryloyloxypropionate (5% by weight) and free radical oligomers and polymers of n-butyl acrylate and phenothiazine.

Example 2

The procedure was as in Example 1 but 55 g/h of cleavage product mixture of the cleavage carried out as follows were additionally fed to the first stirred reactor of the esterification cascade:

In a cleavage apparatus which consisted of a 1 l stirred reactor with a mounted packed column (50 cm (packing height)×2.8 cm (internal diameter), 0.8 cm (diameter) Raschig rings) and a condenser, a mixture of 400 g of the bottom product of the rectification unit III, 100 g of acrylic acid and 20 g of dodecylbenzenesulfonic acid was heated to 195° C. while stirring. 459 g of condensate had been obtained at the top of the packed column within 2 hours. Said condensate comprised 25% by weight of acrylic acid, 29.5% by weight of n-butanol and 43.7% by weight of n-butyl acrylate. The condensate was stabilized by means of 100 ppm of phenothiazine. The cleavage residue was pumpable and substantially free of solids. The cleavage yield was 90% by weight, based on oxyesters contained in the bottom product.

By recycling 55 g/h of cleavage product mixture, it was possible to increase the yield of n-butyl acrylate to 97 mol %, based on so the amount of acrylic acid used in the esterification.

Example 3

The procedure was as in Example 1 but the rectification columns mounted on the stirred reactors of the esterification cascade and the rectification column of the rectification unit II were stabilized not with a solution of phenothiazine in n-butyl acrylate but with a 1% strength by weight solution of phenothiazine in the organic phase of the low-boiler product obtained at the top of the rectification unit II.

No effect of this solvent change on the operation of the plant was observed.

Example 4

The procedure was as in Example 1 but the condensers of the rectification unit were fed with a 0.1% strength by weight solution of phenothiazine in desired ester instead of with an aqueous solution of 4-hydroxy-2,2,6,6-tetramethylpiperidine-N-oxyl. Whereas no polymer formation was detectable even after an operating time of 30 days in the case of N-oxyl stabilization, polymer occurred in the condensate after only 5 days in the case of the phenothiazine stabilization.

Example 5

The procedure was as in Example 1. However, the aqueous phases obtained in the extractive acid separation from the reactor discharge of the reaction zone were combined and were acidified ith sulfuric acid to pH 1, and the acrylic acid present was extracted at 25° C. with various organic extracting agents (25 g of extracting agent per 100 g of combined aqueous phases) in a single stage (separating funnel experiment). Depending on the extracting agent used, the following degrees of extraction were achieved:

| Extracting agent | Degree of extraction |
| --- | --- |
| Mixture of n-butanol and n-butyl acrylate in the weight ratio | |
| 1:3 | 44% |
| 1:1 | 44% |
| 3:1 | 38% |
| organic phase of the low-boiler product at the top of the rectification unit II (LB) | 34% |
| a mixture of LB and n-butanol in the weight | |

-continued

| Extracting agent | Degree of extraction |
|---|---|
| ratio | |
| 1:1 | 57% |
| 6:1 | 54% |

We claim:

1. A process for the continuous preparation of alkyl esters of (meth)acrylic acid by reacting (meth)acrylic acid with alkanols of 1 to 8 carbon atoms in a solvent-free phase at elevated temperatures and in the presence of an acidic esterification catalyst, in which the (meth)acrylic acid, the alkanol and the acid catalyst are fed to a reaction zone, the resulting water as part of a mixture comprising starting alkanol is removed from the reaction mixture by rectification, during the residence time in the reaction zone, in a rectification unit I mounted on the reaction zone, the distillate obtained is separated into an organic phase containing starting alkanol and into a water-containing aqueous phase, the organic phase is recycled to the rectification unit I, the reaction mixture containing the desired ester is passed from the reaction zone into a separation zone comprising further rectification units and the resulting alkyl ester of (meth)acrylic acid is isolated in said separation zone, wherein the (meth)acrylic acid used is an acetic acid-containing crude (meth)acrylic acid, the acidic esterification catalyst is separated from the reaction mixture containing the desired ester before said reaction mixture is passed on into the separation zone comprising further rectification units, the residual reaction mixture I is fed to a rectification unit II and is separated therein by rectification into a low-boiler product containing desired ester and components boiling at a lower temperature than the desired ester and into a residual reaction mixture II comprising the desired ester and components boiling at a higher temperature than the desired ester, at least the organic fraction of the low-boiler product not used as reflux to the rectification unit II is recycled from the rectification unit II into the reaction zone, the residual reaction mixture II is fed to a rectification unit III and the desired ester is separated therein from the components boiling at a higher temperature than the desired ester, the separation efficiency chosen in the rectification unit I is such that the distillate separated off by rectification and comprising water and starting alkanol also contains a portion of the alkyl acetate formed in the reaction zone as a byproduct and only a portion of the organic phase separated from the distillate obtained in the rectification unit I is recycled to the rectification unit I and the remaining amount is separated off as an alkyl acetate purge.

2. A process as claimed in claim 1, wherein the crude (meth)acrylic acid contains up to 5% of its weight of acetic acid.

3. A process as claimed in claim 1, wherein the crude (meth)acrylic acid contains from 0.1 to 3% of its weight of acetic acid.

4. A process as claimed in claim 1, wherein the crude (meth)acrylic acid contains >95% of its weight of (meth) acrylic acid.

5. A process as claimed in claim 1, wherein the alkanol is n-butanol or 2-ethylhexanol.

6. A process as claimed in claim 1, wherein the (meth) acrylic acid used is acrylic acid and the alkanol used is n-butanol.

7. A process as claimed in claim 1, wherein an acidic ion exchanger resin, a mineral acid and/or an organic sulfonic acid is used as the acid esterification catalyst.

8. A process as claimed in claim 1, wherein the acidic esterification catalyst used is sulfric acid.

9. A process as claimed in claim 1, wherein the organic phase separated from the distillate of the rectification unit I comprises at least 5% by weight of alkyl acetate.

10. A process as claimed in claim 1, wherein the organic phase separated from the distillate of the rectification unit I comprises at least 10% by weight of alkyl acetate.

11. A process as claimed in claim 1, wherein the organic phase separated from the distillate of the rectification unit I is recycled with a reflux ratio from 5 to 40 to the rectification unit I.

12. A process as claimed in claim 1, wherein alkanol contained in the organic phase separated off as alkyl acetate purge is extracted from said organic phase by means of water, and the alkanol is then separated from the aqueous phase by stripping and is recycled to the reaction zone.

13. A process as claimed in claim 1, wherein alkanol contained in the aqueous phase of the distillate of the rectification unit I is separated from the aqueous phase by stripping and is recycled to the reaction zone.

14. A process as claimed in claim 1, wherein the rectification unit I is stabilized to prevent undesired free radical polymerization by adding a solution of phenothiazine in alkyl acrylate.

15. A process as claimed in claim 1, wherein, for condensing the distillate, the rectification unit I has a condenser whose cooling walls are stabilized by adding an aqueous solution of a polymerization inhibitor.

16. A process as claimed in claim 15, wherein an aqueous solution containing 4-hydroxy-2,2,6,6-tetramethylpiperidine-N-oxyl is used.

17. A process as claimed in claim 1, wherein that portion of the organic phase obtained in the rectification unit I which is separated off as alkyl acetate purge either a) is incinerated or b) is separated by rectification into a top product comprising mainly alkyl acetate and alkanol and a bottom product comprising mainly alkyl (meth)acrylate and alkanol, and the bottom product is recycled to the reaction zone.

18. A process as claimed in claim 1, wherein that organic fraction of the low-boiler product obtained in the rectification unit II which is not recycled as reflux to the rectification unit II is recycled directly to the reaction zone.

19. A process as claimed in claim 1, wherein the separation of the acidic esterification catalyst from the reaction mixture containing the desired ester is carried out by extraction with water and/or aqueous alkali metal hydroxide solution before said reaction mixture is passed on into the separation zone comprising further rectification units.

20. A process as claimed in claim 19, wherein the aqueous phase obtained in the extraction is first acidified and then subjected to an extraction with a portion of the organic fraction of the low-boiler product obtained in the rectification unit II, as a mixture with alkanol, and the resulting organic extract is recycled to the reaction zone.

21. A process as claimed in claim 1, wherein a portion of the organic fraction of the low boiler product obtained in the rectification unit II is used for the preparation of a phenothiazine solution, and this phenothiazine solution is used for stabilizing the rectification units I and/or II.

22. A process as claimed in claim 1, wherein the bottom product obtained in the rectification unit III is subjected to a cleavage in the presence of a compound of the formula IV
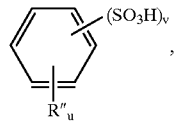
(IV)
where
R", independently of one another, are each alkyl of 6 to 20 carbon atoms,
u is an integer from 1 to 3 and
v is 1 or 2,
and the cleavage products escaping in gaseous form are recycled to the reaction zone.
* * * * *